United States Patent
Klun et al.

(10) Patent No.: US 6,762,339 B1
(45) Date of Patent: Jul. 13, 2004

(54) HYDROPHILIC POLYPROPYLENE FIBERS HAVING ANTIMICROBIAL ACTIVITY

(75) Inventors: Thomas P. Klun, Lakeland, MN (US); Wayne K. Dunshee, Maplewood, MN (US); Kevin R. Schaffer, Woodbury, MN (US); Jeffrey F. Andrews, Stillwater, MN (US); Debra M. Neu, River Falls, WI (US); Matthew T. Scholz, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/572,811

(22) Filed: May 17, 2000

Related U.S. Application Data

(60) Provisional application No. 60/153,626, filed on Sep. 13, 1999, and provisional application No. 60/135,381, filed on May 21, 1999.

(51) Int. Cl.[7] ............................................. A61F 13/00
(52) U.S. Cl. ............................. 602/58; 602/41; 602/42
(58) Field of Search ...................... 602/41–59; 604/358, 604/367, 378, 385.08, 385.23

(56) References Cited

U.S. PATENT DOCUMENTS

| | | |
|---|---|---|
| 2,462,331 A | 2/1949 | Myers |
| 2,732,398 A | 1/1956 | Brice et al. |
| 3,048,263 A | 8/1962 | Sacks |
| 3,048,266 A | 8/1962 | Hackhel et al. |
| 3,285,855 A | 11/1966 | Dexter et al. |
| 3,489,148 A | 1/1970 | Duncan et al. |
| 3,592,194 A | 6/1971 | Duncan |
| 3,644,482 A | 2/1972 | Dexter et al. |
| 3,692,618 A | 9/1972 | Dorschner et al. |
| 3,809,077 A | 5/1974 | Hansen |
| RE28,102 E | 8/1974 | Mayhew |

(List continued on next page.)

FOREIGN PATENT DOCUMENTS

| | | |
|---|---|---|
| BE | 901310 A | 4/1985 |
| CS | 253 423 B | 10/1988 |
| EP | 0 109 126 A | 5/1984 |
| EP | 0 161 757 A2 | 11/1985 |
| EP | 0 395 099 A | 10/1990 |
| EP | 0 455 370 A2 | 11/1991 |
| EP | 0 456 044 A | 11/1991 |

(List continued on next page.)

OTHER PUBLICATIONS

AATCC Technical Manual, 1997, pp. 143 to 44.

T. Klun et al., "Hydrophilic Melt Additives, Synergistic Fluorochemical/Hydrocarbon Surfactant Mixtures," Proceedings of INDA–TEC '97, Cambridge, MA, Sep. 8–10, 1997.

Wente, Superfine Thermoplastic Fibers, 48 INDUS. ENG'G CHEM. 1342–1346 (1956).

Wente et al., Manufacture of Superfine Organic Fibers, Naval Research Laboratories Report No. 4364 (1954).

Projan, Steven J. and Brown–Skrobot, Susan, et al., *Journal of Bacteriology*, Jul. 1994, p. 4204–4209.

J.J. Kabara et al., "Antimicrobial Lipids: Natural and Synthetic Fatty Acids and Monoglycerides," *Antimicrobial Lipids*, vol. 12, No. 9, Sep. 1, 1977, pp. 753–759.

*Primary Examiner*—Kim M. Lewis
(74) *Attorney, Agent, or Firm*—Christopher D. Gram; Nancy M. Lambert

(57) ABSTRACT

Polypropylene fibers and devices that include a fatty acid monoglyceride added to the polypropylene as a melt additive are described. A hydrophilic enhancer material can be advantageously added to the polypropylene as a melt additive to enhance the hydrophilicity of the fibers and devices. An antimicrobial enhancer material can be added to the fibers to enhance the antimicrobial activity.

5 Claims, 1 Drawing Sheet

U.S. PATENT DOCUMENTS

| | | |
|---|---|---|
| 3,847,676 A | 11/1974 | Palmer et al. |
| 3,849,241 A | 11/1974 | Butin et al. |
| 3,860,003 A | 1/1975 | Buell |
| 3,871,378 A | 3/1975 | Duncan et al. |
| 3,971,373 A | 7/1976 | Braun |
| 3,973,068 A | 8/1976 | Weber |
| 4,002,775 A | 1/1977 | Kabara |
| 4,067,997 A | 1/1978 | Kabara |
| 4,073,852 A | 2/1978 | Mesek |
| 4,076,698 A | 2/1978 | Anderson et al. |
| 4,100,324 A | 7/1978 | Anderson et al. |
| 4,181,762 A | 1/1980 | Benedyk |
| 4,189,420 A | 2/1980 | Sugimoto et al. |
| 4,258,097 A | 3/1981 | Benedyk |
| 4,273,802 A | 6/1981 | Kimada et al. |
| 4,273,892 A | 6/1981 | Rave |
| 4,274,971 A | 6/1981 | Hartinger et al. |
| 4,293,460 A | 10/1981 | Marshall et al. |
| 4,296,165 A | 10/1981 | Kakar et al. |
| 4,307,143 A | 12/1981 | Meitner |
| 4,324,246 A | 4/1982 | Mullane et al. |
| 4,340,563 A | 7/1982 | Appel et al. |
| 4,363,891 A | 12/1982 | Rosen et al. |
| 4,426,477 A | 1/1984 | Yasumatsu et al. |
| 4,429,001 A | 1/1984 | Kolpin et al. |
| 4,522,203 A | 6/1985 | Mays |
| 4,540,730 A | 9/1985 | Kieser |
| 4,561,435 A | 12/1985 | McKnight et al. |
| 4,578,414 A | 3/1986 | Sawyer et al. |
| 4,581,397 A | 4/1986 | Witman |
| 4,589,876 A | 5/1986 | Van Tilburg |
| 4,598,004 A | 7/1986 | Heinecke |
| 4,615,937 A | 10/1986 | Bouchette |
| 4,648,876 A | 3/1987 | Becker et al. |
| 4,726,989 A | 2/1988 | Mrozinski |
| 4,734,448 A | 3/1988 | Kasahara et al. |
| 4,762,873 A | 8/1988 | Miyauchi et al. |
| 4,840,738 A | 6/1989 | Hardy et al. |
| 4,857,251 A | 8/1989 | Nohr et al. |
| 4,902,553 A | 2/1990 | Hwang et al. |
| 4,906,687 A | 3/1990 | Modic |
| 4,920,168 A | 4/1990 | Nohr et al. |
| 4,923,914 A | 5/1990 | Nohr et al. |
| 4,933,229 A | 6/1990 | Insley et al. |
| 5,034,008 A * | 7/1991 | Breitkopf ............... 604/385.27 |
| 5,057,262 A | 10/1991 | Nohr et al. |
| 5,064,578 A | 11/1991 | Insley et al. |
| 5,087,520 A | 2/1992 | Suzuki et al. |
| 5,120,888 A | 6/1992 | Nohr et al. |
| 5,145,727 A | 9/1992 | Potts et al. |
| 5,149,576 A | 9/1992 | Potts et al. |
| 5,208,257 A | 5/1993 | Kabara |
| 5,244,724 A | 9/1993 | Antonacci et al. |
| 5,320,772 A | 6/1994 | Tricca |
| 5,346,944 A | 9/1994 | Hayashida et al. |
| 5,362,555 A | 11/1994 | Lal |
| 5,389,374 A | 2/1995 | Brown-Skrobot |
| 5,460,833 A | 10/1995 | Andrews et al. |
| 5,569,461 A | 10/1996 | Andrews |
| 5,614,574 A * | 3/1997 | Sheth ......................... 524/140 |
| 5,618,614 A | 4/1997 | Nohr et al. |
| 5,648,166 A | 7/1997 | Dunshee |
| 5,753,252 A | 5/1998 | Brown-Skrobot |
| 5,763,335 A | 6/1998 | Hermann |
| 5,804,625 A | 9/1998 | Temperante et al. |
| 5,817,325 A | 10/1998 | Sawan et al. |
| 5,854,147 A | 12/1998 | Nohr et al. |
| 5,876,840 A | 3/1999 | Ning et al. |
| 5,882,357 A | 3/1999 | Sun et al. |
| 5,951,993 A | 9/1999 | Scholz et al. |
| 6,316,019 B1 * | 11/2001 | Yang ......................... 424/431 |

FOREIGN PATENT DOCUMENTS

| | | |
|---|---|---|
| EP | 0 674 891 A | 10/1995 |
| EP | 0 937 812 A2 | 8/1999 |
| GB | 0 941 757 A | 11/1963 |
| GB | 2 282 817 a | 4/1995 |
| GB | 2 323 784 A | 7/1998 |
| JP | 4800285 | 3/1973 |
| JP | 48-13737 | 4/1973 |
| JP | 60-28869 | 10/1982 |
| JP | 58-23920 | 2/1983 |
| JP | 59-163477 | 9/1984 |
| JP | 63-309604 | 12/1988 |
| JP | 64-6173 | 1/1989 |
| JP | 2657998 | 8/1990 |
| JP | 2830371 | 1/1992 |
| JP | 4-020571 | 1/1992 |
| JP | 5-11266 | 5/1993 |
| JP | 5-125220 | 5/1993 |
| JP | 11-113780 A | 1/1999 |
| JP | 11-113779 A | 4/1999 |
| LU | 85156 | 12/1983 |
| WO | WO 93/20790 | 10/1993 |
| WO | WO 97/11912 | 4/1997 |
| WO | WO 98/09520 | 3/1998 |
| WO | WO 99/00447 | 1/1999 |
| WO | WO 99/66793 | 12/1999 |

* cited by examiner

HYDROPHILIC POLYPROPYLENE FIBERS HAVING ANTIMICROBIAL ACTIVITY

This application claims the benefit of U.S. Provisional Application No. 60/135,381, filed May 21, 1999, and U.S. Provisional Application No. 60/153,626, filed Sept. 13, 1999, the disclosures of which are both hereby fully incorporated by reference herein.

FIELD OF THE INVENTION

In one aspect, this invention relates to hydrophilic polypropylene fibers which preferably have antimicrobial activity. In another aspect it relates to a multilayer absorbent device suitable as, e.g., a wound dressing, a medical drape, and the like.

SUMMARY OF THE INVENTION

Briefly, in one aspect, the invention provides a polypropylene fiber having incorporated therein a $C_8$ to $C_{16}$ fatty acid monoglyceride or a mixture of glycerides containing at least 80 percent by weight of one or more $C_8$ to $C_{16}$ fatty monoglycerides, and a hydrophilic enhancer material. The invention includes fibrous nonwoven, woven and knit webs and batts made from such fibers.

In another aspect, the invention provides a hydrophilic polypropylene fiber comprising: (a) polypropylene; (b) an effective amount of at least one $C_8$ to $C_{12}$ fatty acid monoglyceride added to the polypropylene as a melt additive to impart both hydrophilicity and antimicrobial activity to Gram-positive bacteria to the surface of the fiber; and (c) an effective amount of an antimicrobial enhancer material such that the surface of the fiber is antimicrobial to Gram-negative bacteria such as *Klebsiella pneumoniae*. Preferred antimicrobial enhancer materials include organic acids and chelating agents, most preferably lactic acid.

In another aspect, the invention provides an absorbent device comprising: (a) an absorbent layer having upper and lower opposed, major surfaces and comprising fibers that are hydrophilic and, preferably, antimicrobial to Gram-positive bacteria; and (b) a liquid-impermeable and moisture vapor permeable backing sheet adhered to the upper surface of the absorbent layer. The fibers comprise polypropylene and an effective amount of at least one $C_8$ to $C_{16}$ fatty acid monoglyceride added to the polypropylene as a melt additive to render the surface of the fibers hydrophilic and, preferably, antimicrobial. In one preferred embodiment of this invention, the surface of the hydrophilic fibers are treated with an effective amount of an antimicrobial enhancer material, such as lactic acid, such that the surface of the fibers in the absorbent layer are antimicrobial to Gram-negative bacteria.

In one embodiment of the absorbent device, the absorbent layer and backing sheet are substantially coextensive. When the absorbent device is used as a wound dressing, it can be positioned over the wound with the absorbent layer positioned adjacent to the wound. The device is then adhered to the skin around the wound, for example, by tape. In another embodiment of the absorbent device, the absorbent layer and the backing sheet are not substantially coextensive and the backing sheet extends beyond at least a portion of the outer perimeter of the absorbent layer to form an extended portion with an upper and lower surface. The lower surface of the extended portion is adjacent to the absorbent layer and at least a portion of the lower surface carries an adhesive layer which can be used to adhere the absorbent device to the skin around the wound. Optionally, this embodiment can further comprise a release liner that is substantially coextensive with the backing sheet and adhered to the backing sheet by the adhesive layer. The release liner would be removed from the absorbent device prior to application to a wound.

A preferred embodiment of the absorbent device further comprises a liquid-permeable sheet that is substantially coextensive with, and adhered to, the lower surface of the absorbent layer. The liquid permeable sheet permits passage of liquid, e.g., exudate, from the wound into the absorbent layer, and preferably prevents adherence of the absorbent layer to the wound. Optionally, the liquid permeable sheet can be hydrophilic or antimicrobial, or both.

The invention also provides useful devices made from such fibers, such as fabrics, webs, batts, and single and multi-layer nonwoven constructions, which are employed in the manufacture of wound dressings, medical drapes, surgical gowns, surgical masks, disposable diapers, filter media, face masks, orthopedic cast padding/stockinettes, respirators, food packaging, dental floss, industrial wipes, textiles, and battery separators. In particular, the absorbent device of the present invention can advantageously be used as a wound dressing because it can (i) absorb a substantial quantity of wound exudate when the dressing is worn for an extended period of time or when the wound produces a large quantity of exudate, and (ii) retard growth of bacteria in the absorbent layer, and, in some cases, in the wound. A further advantage of the absorbent device is that the antimicrobial activity of the device reduces the sterilization load associated with the wound dressing when the device is sterilized prior to packaging such as, for example, by exposure to ethylene oxide.

The invention further provides a method of preparing fibers that are both hydrophilic and, preferably, antimicrobial to Gram-positive and Gram-negative bacteria, the method comprising the steps of (i) preparing a hot melt mixture comprising melted polypropylene and an amount of at least one $C_8$ to $C_{16}$ fatty acid monoglyceride that is effective to impart both hydrophilicity and, preferably, antimicrobial activity to Gram-positive bacteria to the surface of the fiber; and (ii) shaping the mixture into the desired shape, for example forming the fibers by extrusion through a die. When it is desired that the fibers also be antimicrobial to Gram-negative bacteria, the method further comprises the step of contacting the shaped mixture with a liquid composition comprising at least one antimicrobial enhancer material, thereby cooling and at least partially solidifying the shaped mixture and, when present, evaporating sufficient solvent or carrier liquid from the liquid composition to yield an essentially dry coating of the antimicrobial enhancer material on the surface of the shaped mixture that is of sufficient concentration and uniformity such that the extruded surface is antimicrobial to Gram-negative bacteria. When both hydrophilicity and antimicrobial activity are desired, preferably the monoglyceride is a $C_8$–$C_{12}$ fatty acid monoglyceride, such as, for example, glycerol monolaurate. Some embodiments of the aforementioned fibers further incorporate an effective amount of a hydrophilic enhancer material added to the polypropylene as a melt additive to enhance the hydrophilicity of the fibers.

BRIEF DESCRIPTION OF THE DRAWINGS

For a better understanding of the invention, reference may be made to the following description of exemplary embodiments taken in conjunction with the accompanying drawings, in which.

DETAILED DESCRIPTION OF THE INVENTION

Figure 1:
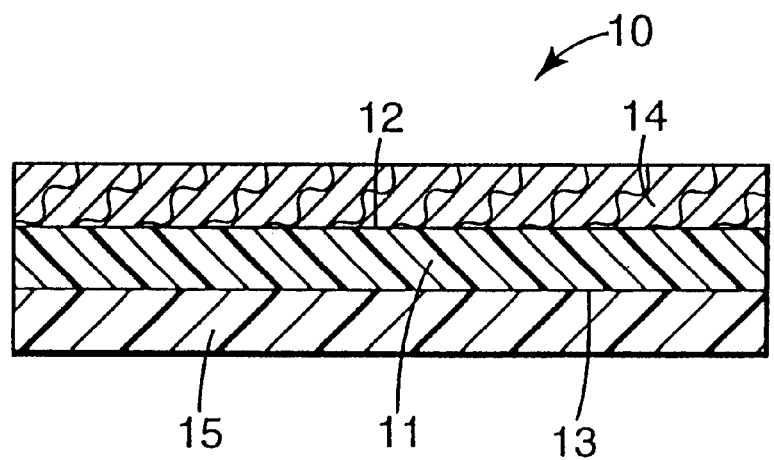
FIG. 1 is a schematic cross-sectional view of an absorbent device according to the invention.

As used herein, "hydrophilic", "hydrophilicity" or similar terminology is used to describe substrates (e.g., fibers, woven or nonwoven fabrics, webs, knits or fiber batts etc.) that can be wet by water, by aqueous solutions of acids and bases (e.g., aqueous potassium hydroxide) and by polar liquids (e.g. sulfuric acid and ethylene glycol).

As used herein, "antimicrobial" or "antimicrobial activity" means that a material has sufficient antimicrobial activity as measured by American Association of Textile and Color Chemists (AATCC) Test Method 100–1993 (AATCC Technical Manual, 1997, pp. 143 to 144), to reduce an initial bacterial load by at least 90% over a 24-hour exposure period at 23–24° C.

The terms "fiber" and "fibrous" as used herein refer to particulate matter, generally comprising thermoplastic resin, wherein the length to diameter ratio of the particulate matter is greater than or equal to about 10. Fiber diameters may range from about 0.5 micron up to at least 1,000 microns and each fiber may have a variety of cross-sectional geometries, may be solid or hollow, and may be colored by, e.g., incorporating dye or pigment into the polymer melt prior to extrusion.

The term "nonwoven web" or "nonwoven fabric" means a web or fabric having a structure of individual fibers which are interlaid, but not in a regular manner, such as knitting and weaving. Nonwoven fabrics or webs have been formed from many processes such as, for example, melt blowing processes, spunbonding processes, and bonded carded web processes.

The term "spunbonded fibers" refers to small diameter fibers which are formed or "spun" by extruding molten thermoplastic material in the form of filaments from a plurality of fine, usually circular, capillaries of a spinneret, and then rapidly reducing the diameter of the extruded filaments, for example, by the methods described in U.S. Pat. Nos. 4,340,563 (Appel et al.) and 3,692,618 (Dorschner et al.). The "spun" fabric is then passed between the rolls of a heated calender to bond the fibers together. Various patterns can be imparted to the fabric by the calender rolls, but the principle purpose of bonding is to increase the integrity of the fabric. The bond area in thermal bonding is usually about 15%, but may vary widely depending on the desired web properties. Bonding may also be accomplished by needling, hydroentanglement, or other methods known in the art.

The term "melt blown fibers" refers to fibers which are typically formed by extruding the molten thermoplastic material through a plurality of fine, usually circular, die capillaries as molten threads or filaments into a high velocity, usually heated gas (e.g., air) stream which attenuates the filaments of molten thermoplastic material to reduce their diameter. Thereafter, the melt-blown fibers are carried by the high velocity gas stream and are deposited on a collecting surface to form a web of randomly disbursed melt-blown fibers. Any of the nonwoven webs may be made from a single type of fiber or two or more fibers which differ in composition and/or thickness. Alternatively, sheath-core fibers can be extruded containing different polymer compositions in each layer, or containing the same polymer composition in each layer but employing the more hydrophilicity-imparting component in the outer sheath layer.

The polymers useful in preparation of the hydrophilic fibers of the present invention are polypropylenes, including isotactic polypropylene, syndiotactic polypropylene, and mixtures of isotactic, atactic and/or syndiotactic polypropylene.

The monoglycerides useful in the invention are derived from glycerol and medium to long chain length (i.e., $C_8$ to $C_{16}$) fatty acids such as caprylic, capric, and lauric acids. Most preferably, the monoglycerides are derived from $C_{10}$ to $C_{12}$ fatty acids and are food grade and Generally Regarded as Safe ("GRAS") materials. Examples of preferred monoglycerides include glycerol monolaurate, glycerol monocaprate, and glycerol monocaprylate. Because the monoglycerides useful in the invention are typically available in the form of mixtures of unreacted glycerol, monoglycerides, diglycerides and triglycerides, it is preferred to use mixtures that contain a high concentration (e.g., greater than about 80%, preferably greater than about 85 wt. %, more preferably greater than about 90 wt. %, and most preferably greater than about 92 wt. %) of the monoglyceride. A convenient way to determine whether one of the aforementioned mixtures, or even a particular monoglyceride, will work in the invention is to calculate the hydrophilic-lipophilic balance ("HLB value") for the mixture. Typically, the HLB value of one of the aforementioned mixtures decreases with increasing fatty acid chain lengths, and also decreases as the diglyceride and triglyceride content in the mixture increases. Useful materials (including pure monoglycerides) typically have HLB values of about 4.5 to about 9, more preferably from about 5.3 to about 8.5. Examples of particularly useful commercially available materials include those available from Med-Chem Laboratories, East Lansing, Mich., under the tradename LAURICIDIN™, Riken Vitamin Ltd., Tokyo, Japan under the tradename POEM™, and Henkel Corp. of Germany under the tradename "MONOMULS™ 90L-12".

Generally, it is difficult to impart hydrophilicity to polypropylene fibers using surfactants. Conventional surfactants typically must be added to polypropylene at higher concentrations than are used in polyethylene, and it is difficult to find effective surfactants that can be used in polypropylene at low concentrations. The impact of the use of high concentrations of conventional surfactants is increased cost, in some instances impairment of the physical properties of the extruded fiber, or impairment of processability of the extrudable polyolefin mixture (e.g., screw slippage, see T. Klun, et al., "Hydrophilic Melt Additives, Synergistic Fluorochemical/Hydrocarbon Surfactant Mixtures," Proceedings of INDA-TEC '97, Cambridge, Mass., Sept. 8–10, 1997). It is quite surprising that the monoglycerides used in this invention can impart good hydrophilicity to polypropylene at concentrations of only about 3 weight percent or less, when typically at least about 5 weight percent of other hydrocarbon surfactants is required to impart acceptable hydrophilicity to polypropylene.

The fibers of this invention can be made by blending or otherwise uniformly mixing at least one $C_8$ to $C_{16}$ fatty acid monoglyceride and the solid polypropylene, for example, by intimately mixing the monoglyceride with pelletized or powdered polymer, and melt extruding the mixture into a fibrous web using any of the commonly known processes for producing nonwoven webs, such as by using the spunbonding techniques or melt-blowing techniques, or combinations of the two, described above. The monoglyceride can be mixed per se with the polypropylene, or it can be mixed with the polymer in the form of a "masterbatch" (concentrate) of the monoglyceride in the polymer. Masterbatches can typically contain from about 10% to as much as about 25% by weight of the monoglyceride. Also, an organic solution of the monoglyceride can be mixed with the powdered or pelletized polymer, the mixture dried to remove solvent, then melted and extruded into the desired shape. Alternatively, the neat form of monoglyceride can be injected into a molten polymer stream to form a blend just prior to extrusion into the desired shape. After extrusion, an annealing step may be carried out to enhance hydrophilicity. Preferably, the article is annealed at a temperature and for a time sufficient to increase the amount of monoglyceride at the surface of the article. Effective time and temperature will bear an inverse relationship to one another and a wide variety of conditions will be suitable. Using polypropylene, for example, the annealing process can be conducted below the melt temperature at about 60° to about 80° C. for a period of about 30 seconds to about 5 minutes or more. In some cases, the presence of moisture during annealing can improve the effectiveness of the monoglyceride. The annealing of a fibrous web can be carried out, for example, in combination with other processing steps for the web (e.g., during the warm cycle of an ethylene oxide sterilization cycle). Hydrophilicity may also be enhanced by contacting the shaped article with heated surfaces, such as hot rolls at about 60° C. to 100° C. for about 10–60 seconds.

Melt-blown hydrophilic fibers useful in the present invention can be prepared as described in U.S. Pat. Nos. 3,849,241 (Butin et al.) and 5,064,578 (Insley et al.), or from microfiber webs containing particulate matter such as those disclosed, for example, in U.S. Pat. Nos. 3,971,373 (Braun), 4,100,324 (Anderson), and 4,429,001 (Kolpin et al.). Multilayer constructions of nonwoven fabrics enjoy wide industrial and commercial utility and include such uses as fabrics for medical gowns and drapes. The nature of the constituent layers of such multilayer constructions can be varied according to the desired end use characteristics, and can comprise two or more layers of melt-blown and spun-bond webs in many useful combinations, such as those described in U.S. Pat. Nos. 5,145,727 (Potts et al.) and 5,149,576 (Potts et al.). In particular, a process similar to that described in Wente, Superfine Thermoplastic Fibers, 48 INDUS. ENG'G CHEM. 1342(1956), or in Wente et al., MANUFACTURE OF SUPERFINE ORGANIC FIBERS, (Naval Research Laboratories Report No. 4364, 1954), can be used for the preparation of the nonwoven webs of this invention. However, because of the potential for thermal instability of the glycerol monoesters employed in the invention as melt additives, it is preferable to incorporate the monoester into the polymer melt just before or just after the die, such as is generally described in U.S. Pat. Nos. 4,933,229 (Insley et al.) and 5,064,578 (Insley et al.).

Preferred hydrophilic enhancer materials include polybutylene, polybutylene copolymers, ethylene/octene copolymers, atactic polypropylene, and certain sorbitan monoesters. Polybutylene and its copolymers, such as, for example, polybutylene 0200, polybutylene 0400, polybutylene 0800, polybutylene DP 8310, and polybutylene DP 8340 (all available from Shell Chemical Co.), ethylene/octene copolymers, such as, for example, ENGAGE™ 8401 and 8402 (available from DuPont Dow Elastomer), ethylene/butylene and butylene/ethylene copolymers, for example, EXACT™ 4023 (available from Exxon) and MONTELL™ dp-8340 (AVAILABLE FROM Montell), and atactic poly(alpha)olefins, such as APAO-2180-E8 atactic polypropylene, a high molecular weight homopolymer of polypropylene, available from Rexene Co., may be incorporated as an additional polymer melt additive to enhance the hydrophilic properties of the extrudate. Effective concentrations of the polybutylene homopolymer and copolymers, determined by measuring the amount incorporated as a melt additive prior to fiber formation, range from about 2 to about 25% by weight, and preferably from about 5% to about 15% by weight. The enhancement effect is seen at polybutylene levels up to about 25% by weight, and at monoglyceride concentrations as low as 1.0% by weight, based on the weight of the composition prior to fiber formation.

$C_8$ to $C_{16}$, preferably $C_{12}$ to $C_{16}$ sorbitan monoesters such as SPAN™ 20 (sorbitan monolaurate) or SPAN™ 40 (sorbitan monopalmitate) for example EXACT™ 4023 (available from Exxon) and MONTELL™ DP-8340 (available from Montell), in combination with the monoglyceride, with or without polybutylene, can further enhance the hydrophilic properties of the extrudate. These monoesters both enhance the hydrophilicity of the web and allow the web to maintain its hydrophilicity after aging at ambient conditions. When these hydrophilic enhancer materials are used, they may replace from about 10% to about 50% of the monoglyceride, preferably from about 30% to about 50%.

In addition to the hydrophilic fibers of the present invention, the nonwoven webs or fabrics and fiber batts can further include commonly used hydrophilic fillers such as, for example, wood pulp, cellulose, cotton, rayon, recycled cellulose, and shredded cellulose sponge, as well as adhesive binders and antistats.

Any of a wide variety of constructions, especially multilayer constructions such as spunbond/melt-blown/spunbond ("SMS") constructions, may be made from the above-described fibers and fabrics, and such constructions will find utility in applications requiring hydrophilicity. Such constructions include aqueous media absorbent devices such as diapers, feminine care products, and adult incontinence products, which utilize the fiber and fabrics as at least a portion of their fluid-absorbing "core" element. "Absorbent device" as used herein refers to a consumer product that is capable of absorbing significant quantities of water and other aqueous fluids (i.e., liquids) such as body fluids. Examples of aqueous media absorbent devices include wound dressings, disposable diapers, sanitary napkins, tampons, incontinence pads, disposable training pants, paper towels, geofabrics, facial tissues, medical drapes and masks, medical gowns, and the like. The fabrics of the present invention are particularly suitable for use in devices like sanitary napkins, diapers, and incontinence pads.

Aqueous media absorbent devices frequently will comprise a substantially aqueous media impervious and moisture vapor-permeable backing sheet, an aqueous media permeable top sheet, and an aqueous media absorbent core comprising at least one aqueous media absorbent layer positioned between said backing sheet and said top sheet. The aqueous media impervious backing sheets may comprise any suitable material, such as polyethylene, polypropylene and polyurethane, preferably having a thickness of at least about 0.020 mm, which will help retain fluid within the absorbent article. The aqueous media impervious backing sheet may also comprise a fabric treated with a water repellent material. The aqueous media permeable top sheets can comprise material, such as polyester, polyolefin, rayon, and the like, that is substantially porous and permits aqueous media to readily pass therethrough into the underlying absorbent core. Suitable materials for both the top sheets and the backing sheets are well known in the art.

More detailed descriptions of sanitary napkins and suitable materials for use therein may be found in U.S. Pat. Nos. 3,871,378 (Duncan et al.), 4,324,246 (Smith et al.), and 4,589,876 (Van Tillberg).

Disposable diapers comprising the hydrophilic fabrics of the invention may be made by using conventional diaper making techniques, replacing or supplementing the wood pulp fiber core typically employed with the fabrics comprising hydrophilic fibers of the present invention. The hydrophilic fibers of the invention may also be used to input hydrophilicity to the top sheet of such an article where hydrophilicity is desired. The hydrophilic fabrics of this invention may thus be used in diapers in single layer or in multiple layer core configurations. Articles in the form of disposable diapers are described by U.S. Pat. Nos. 3,592,194 (Duncan et al.), 3,489,148 (Duncan et al.), and 3,860,003 (Buell).

Preferably, a liquid composition comprising at least one antimicrobial enhancer material and optionally a liquid vehicle is applied by, e.g., dipping, spraying, printing, padding or by brush or sponge, to a portion of or the entire exterior surface of the shaped article, namely, fibers, woven and nonwoven fabrics or webs, and batts. The liquid vehicle is then removed, typically by drying, from the liquid composition to provide an essentially dry coating of the antimicrobial enhancer material containing at least about 50 weight percent enhancer material, preferably at least about 75 weight percent enhancer material, and more preferably at least about 95 wt. % enhancer material on the surface of the article. The antimicrobial enhancer, when combined in sufficient concentration and uniformity with a fiber prepared with the monoglyceride melt additive, enhances either the antimicrobial activity of the article surface or the spectrum of antimicrobial activity, that is, the article surface has antimicrobial activity to both Gram-positive and Gram-negative bacteria. Preferred antimicrobial enhancer materials are organic acids and chelating agents. Examples of suitable antimicrobial enhancer materials include: lactic acid, tartaric acid, adipic acid, succinic acid, citric acid, ascorbic acid, malic acid, mandelic acid, acetic acid, sorbic acid, benzoic acid, salicylic acid, sodium acid pyrophosphate, acidic sodium hexametaphosphate (such as SPORIX™ acidic sodium hexametaphosphate and ethylenediaminetetraacetic acid or EDTA) and salts thereof. Preferred materials are both food grade and GRAS materials, and a particularly preferred antimicrobial enhancer material is lactic acid. Typically, the liquid composition is prepared by dissolving, dispersing or emulsifying the antimicrobial enhancer material in a liquid vehicle such as water and/or a lower alcohol, such as ethanol, to provide a liquid composition comprising from about 1.0 to about 50 wt. % enhancer material based on total weight of the liquid composition. A preferred method for applying the liquid composition to extruded fibers is to spray the hot fibers as they exit the extrusion die. Typical spray rates of about 3 kg/hr to about 25 kg/hr of an aqueous lactic acid solution are suitable for fiber extrusion rates of about 90 to about 100 kg/hr. Undiluted liquid lactic acid or any dilution up to a 1 part lactic acid per 3 parts water are preferred. Solvent removal, if necessary, can be accomplished by drying the coated fibers in an oven.

Turning now to the drawings, in FIG. 1 there is shown an absorbent device 10. The device has an absorbent layer 11 which is substantially conformable and is comprised of one or more layers of nonwoven or woven fabrics, webs or fiber batts. The layers are comprised of fibers that are hydrophilic and, preferably, also antimicrobial to Gram-positive bacteria, and even more preferably, to Gram-negative bacteria as well. Where more than one layer of fabric, web or fiber batt is employed to make the absorbent layer, the layers may be bonded together by melt bonding (e.g., pattern bonding or radio frequency bonding) or adhesives to form a single, unitary layer. Suitable adhesives include hot melt spray adhesives such as HL-1685-X or HL-1710-X, both of which are commercially available from H. B. Fuller Co., St. Paul, Minn. The hot melt adhesive can be applied using spiral spray adhesive systems such as those commercially available from Nordson Corporation, Duluth, Ga. Typical adhesive application rates using such systems are about 6 to 10 grams/m$^2$. In addition, the fibers may be combined with other additives commonly used to prepare absorbent fabrics or batts, such as wood pulp, cellulose, cotton, rayon, recycled cellulose, shredded cellulose sponge and binders. Typically, the thickness of the absorbent layer is from about 0.5 to about 10 mm.

The absorbent layer 11 has an upper surface 12 and a lower surface 13. Adhered to the upper surface 12 is a substantially conformable and substantially coextensive, liquid-impermeable backing sheet 14. The backing sheet 14 can be essentially continuous, or it can be microporous, and preferably it is moisture vapor-permeable so as to prevent an unacceptable buildup of moisture within the absorbent device when the absorbent layer 11 is saturated, for example, with wound exudate. The backing sheet 14 is typically about 0.02 to about 0.12 mm thick, and can be selected from a variety of commonly known polymeric films, such as polyurethane and polypropylene films. A microporous film preferred for use as a backing sheet can be prepared according to the method of U.S. Pat. No. 4,726,989 (Mrozinski), and particularly the procedure described in Examples 1–8 of that patent, without the solvent extraction of the oil. The backing sheet 14 can be adhered to the absorbent layer 11 by melt bonding (e.g., pattern bonding or radio frequency bonding), or by a continuous or discontinuous adhesive layer (not shown) comprising, for example, one of the non-cytotoxic adhesives known in the art such as those described above.

Optionally, a substantially conformable liquid-permeable sheet 15 is adhered to the lower surface 13 of the absorbent layer 11. By "adhered" is meant that sheet 15 abuts and extends along the lower surface 13 and can be, but need not be, attached thereto by adhesive means. The liquid-permeable sheet 15 is preferably substantially coextensive with the absorbent layer 11 and adhered to it either by melt bonding or by an adhesive as described hereinabove (e.g., a hot melt spray adhesive). Typically, the liquid-permeable sheet is about 0.05 mm to about 0.075 mm thick, and is substantially porous to permit free flow of liquid. A particularly preferred liquid-permeable sheet is the non-stick netting commercially available from Applied Extrusion Technologies, Middletown, Del. as Delnet CKX215 P-S or Delnet P530-S.

Figure 2:
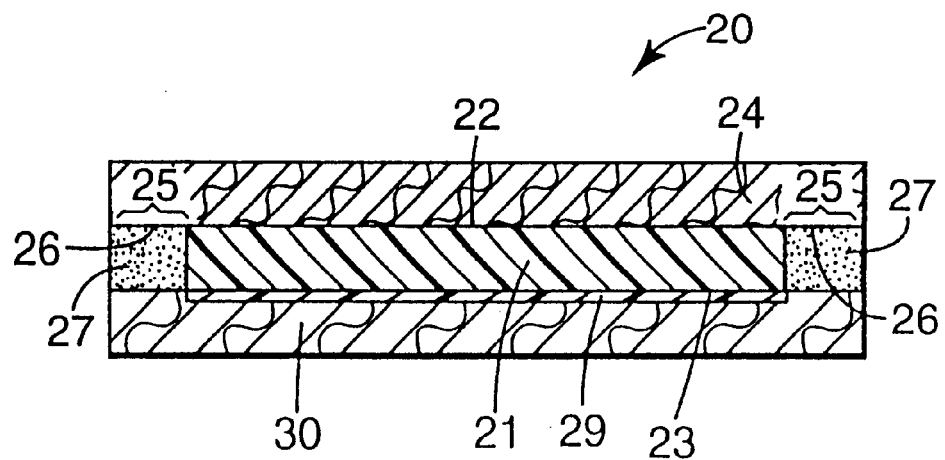
FIG. 2 is a schematic cross-sectional view of another absorbent device according to the invention.

Another embodiment of the absorbent device is depicted in FIG. 2. Shown in FIG. 2 is an absorbent device 20. The device 20 has an absorbent layer 21 with an upper surface 22 and lower surface 23. Adhered to the upper surface 22 of the absorbent layer 21 is a substantially conformable backing sheet 24. However, in this embodiment, the backing sheet 24 is not coextensive with the absorbent layer 21. Instead, the backing sheet 24 extends beyond the outer perimeter of the absorbent layer 21, preferably uniformly, to provide an extended portion 25 with a lower surface 26. The lower surface of the extended portion 25 carries an adhesive layer 27 that can be used to adhere the absorbent device to the target, such as the skin around a wound. The adhesive 26, preferably a pressure sensitive adhesive, may be in the extended portion 25 or may be covering the entire surface 22. Preferred adhesives include adhesives having good adhesion to skin and resistance to moisture. Examples of such adhesives are those described in U.S. Pat. No. 5,648,166 (Dunshee).

Optionally, the device also includes a substantially conformable, liquid-permeable sheet 29 adhered to the lower surface 23 of the absorbent layer 21. Most preferably, the liquid permeable sheet 29 is coextensive with the absorbent layer 21. The device also optionally includes a release liner 30 that is substantially coextensive with and adhered to the backing sheet 24 by the adhesive layer 27. Prior to application of the absorbent device 20 to the target, the release liner 30 is removed from the absorbent device. Examples of suitable adhesives for adhesive layer 27 include any of the non-cytotoxic adhesives described hereinabove. Release liner 30 can be any polymeric film, paper or foil known in the art to be useful as a release liner. Examples of useful release liners include 50 g/m$^2$ basis weight SC 501FM40 white Sopal Flexible Packaging available from Day Cedex, France. The backing sheet 24, absorbent layer 21, and liquid permeable sheet 29 can be the same as those elements used in the absorbent device depicted in FIG. 1. However, moisture vapor-permeable adhesive coated films like those described in U.S. Pat. No. 4,726,989 can also be used as the backing sheet 24.

The invention may also find particular utility as an antimicrobial face mask, e.g., a surgical mask, or as an antimicrobial medical drape or gown, e.g., a surgical drape. Face masks are used as barriers between the wearer and the environment, and are well described in the art, e.g., in U.S. Pat. No. Re. 28,102 (Mayhew). Through their filtration efficiency, face masks can remove particulates (organic, inorganic, or microbiological) from the incoming or out going breath. Face masks are generally not antimicrobially active even though they are commonly used in a health care setting as a method of minimizing pathogen transmission risk. The invention includes a face mask with antimicrobial activity, that is a mask capable of killing microorganisms that come into contact with it. This activity extends to antimicrobial kill of such common organisms like bacteria, fungi, the influenza A virus, and the rhinovirus, the cause of the common cold. Surgical drapes may be constructed from single layers of a fibrous web material or include multi-layered laminates that include one or more film layers, e.g., as described in U.S. Pat. Nos. 3,809,077 (Hansen) and 4,522,203 (Mays). Surgical drapes require sterilization prior to use and since the drapes generally do not have inherent antimicrobial activity, any microbial contamination can remain on the surface of these drapes.

The invention includes surgical drapes that can be self-sterilizing through the application of an antimicrobial coating to the surface of the surgical drape. Active surfaces like the self-sterilizing surgical drapes of this invention can provide long term antimicrobial kill of microorganisms coming in contact with the drape surface. The following examples are offered to aid in understanding of the present invention and are not to be construed as limiting the scope thereof. Unless otherwise indicated, all parts and percentages are by weight.

Glossary

Hydrocarbon Surfactants

GML: glycerol monolaurate, available from Med-Chem Laboratories, East Lansing, Mich. under the tradename "LAURICIDIN™."

GM-C8: glycerol monocaprylate, available as POEM™ M-100 from Riken Vitamin LTD, Tokyo, Japan.

GM-C10: glycerol monocaprate, available as POEM™ M-200 from Riken Vitamin LTD., Tokyo, Japan.

GM-C12: glycerol monolaurate, prepared as follows: A 250-mL three-necked flask equipped with thermometer, addition funnel and nitrogen inlet adapter was charged with 100.16 g (0.5 mol) of lauric acid (available from. Sigma-Aldrich Co., Milwaukee, Wis.) and 0.7 g (0.5% with respect to the total weight of reactants) of benzyl triethylammonium chloride (the catalyst, available from Sigma-Aldrich Co.). The reaction mixture was heated to an internal temperature of 114° C. using a silicone oil bath at 119° C. Next, 38.89 g (0.525 mol) of glycidol (available from Sigma-Aldrich Co.) was added at a constant rate over 22 minutes with the internal temperature rising to a maximum of 130° C. at 20 minutes. Within 1.5 hours, the temperature of the reaction had fallen to 113° C. At 6.5 hours, the reaction was stopped and 134.19 g of product was isolated. The product was analyzed by $^1$H and $^{13}$CNMR spectroscopy, and the ratios of products were established by assignment and quantitative integration of the glycerol carbons.

GM-C14: glycerol monomyristate, prepared as follows: Using a procedure similar to that described for the preparation of GM-C12, 114.19 g (0.5 mol) of myristic acid (available from Sigma-Aldrich Co.), 38.9 g (0.525 mol) of glycidol, and 0.77 g of benzyl triethylammonium chloride were reacted for 18 hours to provide 143.5 g of product.

GM-C16: glycerol monopalmitate, prepared as follows: Using a procedure similar to that described for the preparation of GM-C12, 89.75 (0.35 mol) of palmitic acid (available from Sigma-Aldrich Co.), 27.22 g (0.3675 mol) of glycidol, and 0.58 g of benzyl triethylammonium chloride were reacted for 6 hours to provide 114.4 g of product.

GM-C18: glycerol monostearate, prepared as follows: Using a procedure similar to that described for the preparation of GM-C12, 142.24 (0.5 mol) of stearic acid (available from Sigma-Aldrich Co.), 36.67 (0.495 g mol) of glycidol, and 0.895 g of benzyl triethylammonium chloride were reacted for 18.5 hours to provide approximately 170 g of product.

GM-C18D: glycerol monostearate, prepared as follows: An aliquot of about 60 g of GM-C18 was distilled using a single plate distillation at a head temperature of 240° C. at 0.5 torr to provide about 25 g of distillate.

HS-1: glycerol monococoate, available as LUMULSE™ GML from Lambert Technologies, Skokie, Ill.

HS-2: glycerol monooleate, available as LUMULSE™ GMO from Lambert Technologies.

HS-3: glycerol monostearate, available as EMEREST™ 2400 from Henkel Corp., Organic Products Division, Charlotte, N.C.

HS-4: glycerol monoisostearate, prepared as follows: A 1-L 3-necked round bottom flask equipped with heating mantle, stirrer, thermometer, and Dean-Stark apparatus was charged with 284.48 g (1 mol) of isostearic acid (available as EMEREST™ 873 from Henkel Corp.), 92.09 g (1 mol) of glycerol, 2.26 g of p-toluenesulfonic acid (available from Sigma-Aldrich Chemical Co., Milwaukee, Wis.), and 131.8 g of toluene. The resulting mixture was stirred and heated overnight, using Dean-Stark conditions, was allowed to cool to 80° C., was neutralized with 1.75 g of triethanolamine, and was filtered through a Buchner funnel containing a pad of CELITE™ filtering medium (available from Aldrich Chemical Co., Milwaukee, Wis.). The filtrate was concentrated by removing solvent at 150° C. and 40 torr pressure to provide an amber liquid product.

HS-5: PEG 600 dioleate, available as MAPEG™ 600DO from BASF Corp., Specialty Chemicals; Mount Olive, N.J.

HS-6: PEG 400 monotallate, available as MAPEG™ 400MOT from BASF Corp., Specialty Chemicals.

HS-7: ethoxylated (9.5) octylphenol, available as TRITON™ X-100 from Union Carbide Corp, Danbury, Conn.

HS-8: polyoxyalkylene (10) oleyl ether, available as BRIJ™ 97 from ICI Surfactants, Wilmington, Del.

HS-9: a phenoxyaryl alkyl ethoxylate, available as EMULVIN™ from Bayer Corp., Pittsburgh, Pa.

SPAN™ 20: sorbitan monolaurate, 100% active, having an HLB of 8.6, available from Uniquma (ICI Surfactants), Wilmington, Del.

SPAN™ 40: sorbitan monopalmitate, 100% active, having an HLB of 6.7, available from Uniquma (ICI Surfactants), Wilmington, Del.

ARLACEL™ 60: sorbitan monostearate, 100% active, having an HLB of 4.3, available from Uniqema (ICI Surfactants).

ARLACEL™ 83: sorbitan sequioleate (1½ mole adduct), 100% active, having an HLB of 3.7, available from Uniqema (ICI Surfactants).

Fluorochemical Surfactants

FS-1: a hydrophilic fluorochemical polymer melt additive for nonwovens, available as 3M™ FC-1802 Protective Chemical from 3M Company, St. Paul, Minn.

FS-2: MeFOSA/TRITON™ X-100 adduct, made by the condensation reaction of TRITON™ X-100 chloride with MeFOSA amide ($C_8F_{17}SO_2NH_2$) as follows:

First, TRITON™ X-100 chloride was made according to the following procedure: To a 3-necked round bottom flask equipped with overhead stirrer, thermometer, reflux condenser and two attached gas washing bottles (the second bottle containing a 10% aqueous solution of sodium hydroxide) was charged 646 g (1.0 mol) of TRITON™ X-100 and 12.9 g of CELITE™ filtering medium. The resulting mixture was heated to 60° C., then 142.76 g (1.2 mol) of thionyl chloride was added via an addition funnel over a period of about 22 minutes, raising the reaction mixture temperature to 75° C. Then nitrogen was bubbled through the reaction mixture for 4 hours, during which time the mixture temperature varied from 68–71° C. The reflux condenser and gas washing bottles were replaced by a still head, and the reaction mixture was stirred while a vacuum of about 50 torr absolute pressure was applied. After the reaction was shown to be complete by $^{13}C$ and $^1H$ NMR analysis, the reaction mixture was filtered hot through a C-porosity fritted glass Buchner funnel to yield a light yellow product, TRITON™ X-100 chloride.

The TRITON™ X-100 chloride was then reacted with MeFOSA using the following procedure. To a 3-necked round bottom flask equipped with overhead stirrer, reflux condenser and nitrogen inlet adapter was charged 125 g (0.244 eq) of MeFOSA (which can be made as described by Brice et al. in U.S. Pat. No. 2,732,398), 177.80 g of TRITON™ X-100 chloride, 30.18 (0.2794 eq) of sodium carbonate and 2.46 g (0.0149 eq) of potassium iodide. The resulting reaction mixture was heated to 120° C. for 8 hours, at which time the MeFOSA had disappeared according to gc analysis. After cooling to 95° C., the reaction mixture was washed with 157 g of 10% aqueous sulfuric acid, followed by 157 g of deionized water. The washed reaction mixture was concentrated by evaporation on a rotary evaporator at 70° C. and 50 torr absolute pressure to give 252.6 g of a brown liquid (92.2% yield). The structure of the desired product was confirmed by $^{13}C$ and $^1H$ NMR spectroscopy.

Silicone Surfactant

SS-1: NUWET™ 500 silicon ethoxylate, available from Osi Specialties, Inc., Danbury, Conn.

Thermoplastic Polymers

PP 3505: ESCORENE™ PP3505 polypropylene, having a 400 melt index flow rate, available from Exxon Chemical Co., Baytown, Tex.

PP 3746: ESCORENE™ PP3746 polypropylene, having a 1400 melt index flow rate, available from Exxon Chemical Co.

EOD 96-36: FINA™ EOD-96-36 polypropylene, having a 750 melt flow index, available from Fina Corp., La Porte, Tex.

3960X: FINA™ 3960X polypropylene, having a 350 melt flow index, available from Fina Corp., La Porte, Tex.

3155: EXXON™ 3155 polypropylene, having a 35 melt flow index, available from Exxon Chemical co.

4023: EXACT™ 4023 ethylene/butylene copolymer, containing a majority by weight of ethylene, available from Exxon Chemical Co.

PB 0400: MONTELL™ 0400 1-butylene homopolymer, having a 20 nominal melt index, available from Montell, Houston, Tex.

DP-8910: MONTELL™ DP-8910 polybutylene, containing peroxide, available from Montell.

DP-8340: MONTELL™ DP-8340 1-butylene/ethylene copolymer, having a melt flow index of 35, available from Montell.

8401: ENGAGE™ 8401, an ethylene/octene copolymer containing 19% octene by weight, having a melt flow index of 30, available from DuPont Dow Elastomer. 8402: ENGAGE™ 8402, an ethylene/octene copolymer containing 13.5% octene by weight, having a melt flow index of 30, available from DuPont Dow Elastomer.

Antimicrobial Enhancer Material

LA: Lactic acid, USP, commercially available from J. T. Baker, Phillipsburg, N.J.

Analyses and Test Methods

Analyses and Calculated Hydrophilic-Lipophilic Balance (HLB) Values of Glycerol Monoesters Table 1 provides the weight percent of monoglycerides, diglycerides, triglycerides, and glycerol present in a number of the materials described in the glossary. The mole percent values of the materials were established by assignment and quantitative integration of the glycerol carbons in the $^{13}C$ NMR spectrum of each material, and the mole percent values were translated into weight percent values. The amounts of 1- and 2-substituted monoglycerides as well as the amounts of the 1,2- and 1,3-diglycerides were combined to determine, respectively, the weight percent fractions of monoglycerides, and diglycerides presented in the table.

Also presented in Table 1 are calculated HLB values for each material. The HLB values for each monoglyceride, diglyceride and triglyceride present in the materials were calculated using a group contribution method. The HLB value for glycerol was also calculated. In this method, HLB values are derived using the relation:

HLB=7+Σ(hydrophilic group number)−Σ(hydrophobic group number). The group numbers for the particular monoglycerides, diglycerides and triglycerides as well as glycerol are given in Tables I–IV on page 374 of the reference: J. T. Davies and E. K. Rideal, *Interfacial Phenomena*, Second Edition, Academic Press, London, 1963.

The HLB value for each material was then calculated using the weight fraction of glycerol and each monoglyceride, diglyceride and triglyceride component in the material using the following equation:

HLB mixture=(wt. fraction monoglyceride)×(*HLB* monoglyceride)+(wt. fraction diglyceride)×(*HLB* diglyceride)+(wt. fraction triglyceride)×(*HLB* triglyceride)+(wt. fraction glycerol)×(*HLB* glycerol)

obtained. The process condition for each mixture was the same, including the melt blowing die construction used to blow the microfiber web. The basis weight of the resulting webs, unless otherwise stated, was 50±5 g/m² (GSM), and the targeted diameter of the microfibers was 7 to 12 micrometers. The width of the web was about 12 inches (30.5 cm). Unless otherwise stated, the extrusion temperature was 255° C., the primary air temperature was 258° C., the pressure was 124 KPa (18 psi), with a 0.076 cm air gap width, and the polymer throughput rate was about 180 g/hr/cm.

The measured average effective fiber diameter for each type of polymer used in the Examples was as follows:

| | |
|---|---|
| PP 3505: | 7.5 to 12.0 microns |
| EOD 96-36 polypropylene: | 7.4 to 11.4 microns |

Melt-Blown Extrusion Procedure B

This Procedure B is basically the same as Procedure A described above, except that the extrusion temperature was 280 to 350° C., the polymer throughput rate was about 66

TABLE 1

| Glossary Designation | Monoglyceride Component of Surfactant | # Carbons in Monoglyceride Fatty Acid | Monoglycerides (wt. %) | Diglycerides (wt. %) | Triglycerides (wt. %) | Glycerol (wt. %) | Weight % Total | Calculated HLB Mixture |
|---|---|---|---|---|---|---|---|---|
| GM-C8 | Glycerol monocaprylate | 8 | 88.8 | 7.4 | 0.0 | 3.8 | 100 | 8.3 |
| GM-C10 | Glycerol monocaprate | 10 | 89.1 | 6.5 | 0.0 | 4.4 | 100 | 7.4 |
| GML | Glycerol monolaurate | 12 | 94.0 | 5.7 | 0.0 | 0.3 | 100 | 6.3 |
| GM-C12 | Glycerol monolaurate | 12 | 90.5 | 8.3 | 0.0 | 1.1 | 100 | 6.2 |
| HS-1 | Glycerol monococoate | 12 | 44.5 | 38.0 | .3 | 8.3 | 100 | 4.3 |
| GM-C14 | Glycerol monomyristate | 14 | 88.4 | 6.8 | 1.2 | 3.6 | 100 | 5.3 |
| GM-C16 | Glycerol monopalmitate | 16 | 93.8 | 4.3 | 0.0 | 1.8 | 100 | 4.5 |
| GM-C18 | Glycerol monostearate | 18 | 87.7 | 6.4 | 2.7 | 3.2 | 100 | 3.0 |
| GM-C18D | Glycerol monostearate | 18 | 92.3 | 4.5 | 0.0 | 3.2 | 100 | 3.6 |
| HS-3 | Glycerol monostearate | 18 | 56.5 | 35.1 | 2.0 | 6.4 | 100 | 1.2 |
| HS-2 | Glycerol monooleate | 18 | 50.9 | 41.1 | 4.2 | 3.9 | 100 | 0.2 |

Effective Fiber Diameter (EFD) Measurement

EFD measurements were made according to the procedure outlined in Davies, C. N., "The Separation of Airborne Dust and Particles", Institute of Mechanical Engineers, London, Proceedings 1B, 1952.

Melt-Blown Extrusion Procedure A

This melt-blown extrusion procedure was the same as described in U.S. Pat. No. 5,300,357 (Gardiner), at column 10. A Brabender 42 mm conical twin screw extruder was used, with a maximum extrusion temperature of 255° C. and distance to the collector of 12 inches (30 cm). Monoglyceride and polypropylene mixtures were prepared by blending the monoglyceride and polypropylene in a paperboard container using a mixer head affixed to a hand drill for about one minute until a visually homogeneous mixture was kg/hr, and the monoglyceride was incorporated into the polymer melt stream just before the die, as described in U.S. Pat. Nos. 4,933,229 (Insley et al.) and 5,064,578 (Insley et al.). The monoester throughput rate was about 2 kg/hr and the die width was about 152 cm.

Spunbond Extrusion Procedure

The extruder used was a Reifenhauser Extruder Model Number RT 381 (available from Reifenhauser Co., Troisdorf, Nordrheim Westfalen, Germany), 2.34 m in length×1.335 m in width×1.555 m in height, weighing 2200 kg. The extruder was driven by an infinitely variable shunt wound DC motor, 37.3 kW and 2200 rev/min max. The maximum screw speed was reduced to 150 rev/min. The screw was 70 mm in diameter and 2100 mm in length. The extruder had five 220 V heating zones using a total of 22.1 kW of heating power. The metering pump delivered 100 cm³ of polymer melt per revolution. The die had seven adjacent heating zones. The spinneret was approximately 1.2 meters wide and had 4036 holes, each hole of 0.6 mm diameter and 2.4 mm in length. The extrusion temperature reported was the temperature in the die block before the polymer melt stream was distributed along the die. The maximum throughput of the die was 104 kg/h, or 0.43 g/hole/min. The cooling chamber operated with an air temperature of 18.3° C. and a cooling air speed of 1000 to 3000 n/min.

The bonder used to bond the spunbond fibers into a fabric was a Kusters Two-Bowl-Thermobonding-Calender (available from Kusters Corp., Nordrheim Westfalen, Germany). The effective bonding width was 1.2 m. The upper patterned metal roll had a 14.66% bonding area and a temperature of 270–285° F. (132–141° C. ), while the lower rubber roll had a slick surface and a temperature of 265–280° F. (129–138° C. ). The bonding nip pressure was 57–750 pounds force per linear inch (3000–41000 J/cm). The heating of the rolls was done by convection from a continuously circulating furnace oil. The temperature of the nips was 200–300° F. (93–149° C.). The speed of the bonder was directly synchronized to the speed of the collection belt that had a range of 3.6 to 65 linear meters per minute.

The basis weight for each nonwoven fabric (g/m$^2$) was calculated by multiplying the speed of the spin pump (rev/m) times the constant 71. For all examples, the basis weight used was approximately 20 g/m$^2$.

Hydrophilicity Test

The Hydrophilicity Test was run by holding the outside surface (side opposite the collector) a rectangular nonwoven web sample approximately 8×11 inches (20×28 cm) under a stream of either hot (approximately 45°±2° C. ) or cold (approximately 25°±2° C.) tap water with a volume output of approximately 200 ml/min at a distance of about 1 inch (2.5 cm) from the water spigot. The nonwoven web sample was held with thumbs downward on top of the center of each 8 inch (20 cm) side edge and fingers upward underneath the web sample pointed toward the center of the sample for support, and tilting the web slightly so that the far 11 inch (28 cm) edge was slightly higher than the near 11 inch (28 cm) edge. Each nonwoven web sample had a basis weight of 50±5 g/m$^2$, an effective fiber diameter of 8 to 13 microns (as calculated according to the method set forth in Davies, C. N., "The Separation of Airborne Dust and Particulates," Institution of Mechanical Engineers, London, Proceedings 1B, 1952), and a web solidarity of 5 to 15%. The following number scale was used to rate the hydrophilicity of each web sample:

1 immediate wetting (web sample goes from being completely opaque to completely translucent);

2 wetting delayed for about 0.5 to 2.0 seconds (web sample goes from being completely opaque to completely translucent);

3 wetting delayed from greater than 2.0 seconds to about 10 seconds (web sample goes from being completely opaque to completely translucent);

4 wetting delayed from greater than 2.0 seconds to about 10 seconds, but wetting occurs only where the web sample contacts the hand placed under the sample;

5 no wetting at all (i.e., the web sample remains opaque). Where the degree of wetting varied across the width of the web sample, a set of several number values was recorded, representing values measured in a direction perpendicular to the machine direction from one side of the web sample to the other. For example, in one case, the first 40% of the distance across the web sample showed a reading of "1", the next 20% of the distance across the web sample showed a reading of "5", and the final 40% of the distance across the web sample showed a reading of "2". The reported rating for this web would be the weighted average of the values or (0.40) (1)+(0.20)(5)+(0.40)(2)=2.2.

A value (either single or weighted average) of no greater than 3 for both hot and cold water is preferred.

Percent Wet Pickup Test

A 12 inch (30 cm) long×8 inch (20 cm) wide by 2 inch (5 cm) deep pan was filled with 2 liters of tap water having a temperature of 25±2° C. Nonwoven melt blown fabric web samples having a target basis weight of 9 to 10 grams per square meter were each cut to a rectangular shape of 6.5±0.5 inches by 11.5±1 inch and weighed 2.4±0.3 grams. Each rectangular web sample was weighed to the nearest hundredth gram on a balance to give the Fabric Dry Weight. The web sample was placed flat upon the water surface for 5±2 seconds, then was removed from the water surface and was allowed to drip excess water for 5±2 seconds. The wetted, drained web sample was weighed again to the nearest 0.01 gram to give the Fabric Wet Weight. The Percent Wet Pickup was calculated using the formula:

$$\text{Percent Wet Pickup} = \frac{(\text{Fabric Wet Weight} - \text{Fabric Dry Weight})}{\text{Fabric Dry Weight}} \times 100$$

The test was repeated on five different samples for each test web, so that each Percent Wet Pickup value reported is the average of five replications. The standard deviation is given for each set of five replications.

Percent Water Absorbency Test

Evaluation of the percent water absorbency of various materials of this invention was measured using the following test procedure. For each test, a 7.62 cm×7.62 cm sample having a target basis weight of 9 to 10 grams per square meter was weighed, placed on the surface of tap water at 32°±2° C. for one minute, and then removed from the surface of the water by holding up a corner of the pad with the smallest possible area. When the sample used was a pad having a waterproof side, the absorbent side (i.e., netting side) of the pad was placed down on the water surface. The excess water was allowed to drip off from one corner of the pad for 30±2 seconds, still holding a corner of the pad with the smallest possible area. The sample was then weighed again. The percent water absorbency of the sample was then calculated using the formula:

$$\text{Percent Water Absorbency} = \frac{(\text{Wet Sample Weight} - \text{Dry Sample Weight})}{\text{Dry Sample Weight}} \times 100$$

Each Percent Water Absorbency reported value is the average of 8–10 replications.

Drop Wetting Test

The hydrophilicity of the outside surface (side opposite the collector belt) of spunbond fabrics was measured using the following drop wetting test procedure. A 10 cm by 20 cm piece of spunbond fabric, having a basis weight of approximately 20 g/m$^2$ unless otherwise noted, was placed on a double folded paper towel, and the fabric was smoothed by hand to be in as intimate contact as possible with the paper towel. Next, 10 drops of 0.9% aqueous NaCl having a temperature of 25±3° C. and about 6–8 mm in diameter were gently placed on the fabric at least 8 mm apart. After 10 seconds, the number of drops that are completely absorbed from the surface of the nonwoven into the paper towel was recorded. Values provided in the examples are each an average of three such drop absorption trials.

Antimicrobial Test

The materials of this invention were cut into 3.8 cm×3.8 cm square samples and evaluated for antimicrobial activity according to the American Association of Textile and Color Chemists (AATCC) Test Method 100–1993, as published in the AATCC Technical Manual, 1997, pages 143–144. Modifications to the Test Method included the use of Tryptic Soy Broth as the nutrient broth and for all dilutions and Tryptic Soy Agar as the nutrient agar. Letheen Broth (VWR Scientific Products, Batavia, Ill.) was used as the neutralizing solution.

EXAMPLES

Examples 1–13 and Comparative Examples C1–C15

In Examples 1 to 7, the initial wettability of nonwoven webs prepared using Melt-Blown Extrusion Procedure A to extrude EOD 96-36 polypropylene with various melt additives was determined.

Examples 1 to 7 were prepared using concentrations of GML varying from 1 to 4% by weight (based on polymer weight). Examples 8–13 were prepared using various monoglycerides of relatively high purity at 3% by weight. Comparative Example C1 was prepared using glycerol monostearate at 3% by weight. Comparative Examples C5 to C8 were prepared using less pure grades of glycerol monoesters. Comparative Examples C2 and C3 were prepared using different fluorochemical nonionic surfactants and Comparative Example C4 was prepared using a silicone surfactant. Comparative Examples C9 to C13 were prepared using various other hydrocarbon surfactants, including PEG di- and monoesters, an alkylphenol ethoxylate, an alcohol ethoxylate, and a phenoxy aryl alkylphenol ethoxylate. Comparative Examples C14 and C15 were prepared without a melt additive. It should be noted that Examples 8–10 and Comparative Example C15 were prepared using the same Melt-Blown Extrusion Procedure A outlined above, but at an extrusion temperature of 220° C. instead of 255° C. A rating of hydrophilicity for each nonwoven web was determined using the Hydrophilicity Test. A description of the samples and their Hydrophilicity Test results are summarized in Table 2.

Also included in Table 2 is an analysis of weight percent monoglyceride, where applicable, for each additive.

TABLE 2

| Ex. | Surfactant 1 (wt. %) | Monoglyceride in Surfactant 1 (wt. %) | Cold Water Rating | Hot Water Rating |
|---|---|---|---|---|
| 1 | GML (1.0%) | 94 | 5.0 | 3.4 |
| 2 | GML (1.25%) | 94 | 4.4 | 1.9 |
| 3 | GML (1.5%) | 94 | 2.3 | 1.3 |
| 4 | GML (2.0%) | 94 | 1.4 | 1.0 |
| 5 | GML (2.5%) | 94 | 1.3 | 1.0 |
| 6 | GML (3.0%) | 94 | 1.0 | 1.0 |
| 7 | GML (4.0%) | 94 | 1.0 | 1.0 |
| 8* | GML (3.0%) | 94 | 1.0 | 1.0 |
| 9* | GM-C8 (3.0%) | 88.8 | 1.7 | 1.4 |
| 10* | GM-C10 (3.0%) | 89.1 | 1.0 | 1.0 |
| 11 | GM-C12 (3.0%) | 90.5 | 1.2 | 1.0 |
| 12 | GM-C14 (3.0%) | 88.4 | 2.7 | 1.0 |
| 13 | GM-C16 (3.0%) | 93.8 | 4.4 | 1.0 |
| C1 | GM-C18 (3.0%) | 87.0 | 5.0 | 3.2 |
| C2 | FS-1 (1.25%) | N/A | 1.0 | 1.0 |
| C3 | FS-2 (1.25%) | N/A | 3.0 | 1.0 |
| C4 | SS-1 (3.0%) | N/A | 5.0 | 3.0 |
| C5 | HS-1 (3.0%) | 44.5 | 5.0 | 4.6 |
| C6 | HS-2 (3.0%) | 50.9 | 5.0 | 5.0 |
| C7 | HS-3 (3.0%) | 56.5 | 5.0 | 5.0 |
| C8 | HS-4 (3.0%) | N/M | 5.0 | 5.0 |
| C9 | HS-5 (3.0%) | N/A | 5.0 | 5.0 |
| C10 | HS-6 (3.0%) | N/A | 5.0 | 3.3 |
| C11 | HS-7 (3.0%) | N/A | 5.0 | 5.0 |
| C12 | HS-8 (3.0%) | N/A | 5.0 | 4.0 |
| C13 | HS-9 (3.0%) | N/A | 5.0 | 5.0 |
| C14 | — | N/A | 5.0 | 5.0 |
| C15* | — | N/A | 5.0 | 5.0 |

N/M: means not measured
N/A: means not applicable because material did not contain monoglyceride
*: means extruded at 220° C. rather than the usual 270–280° C.

The data in Table 2 show that samples prepared using GML provided good wettability even at GML levels as low as 1.5% in the polymer. At the 3% level, excellent wettability to both cold and hot water resulted, and the overall performance of the sample favorably compared to samples prepared using FS-1, a more expensive hydrophilic fluorochemical additive. Even at some levels less than 3%, GML outperformed SS-1, a hydrophilic silicone surfactant.

The data also show that materials containing monoglycerides derived from $C_8$, $C_{10}$, $C_{10}$, $C_{12}$, $C_{14}$ and $C_{16}$ carboxylic acids (HLB values of 8.3, 7.4, 6.3, 6.2, 5.3 and 4.5 respectively) also imparted improved wettability to nonwoven webs. However, materials containing monoglycerides derived from $C_{18}$ carboxylic acid provided only slightly better hot water wetting than the control.

The effect of the concentration of monoglyceride in the surfactant material is illustrated by comparing Examples 6 and 11 (prepared from GML and GM-C12, which have glycerol monolaurate contents of 94 and 90.5% and calculated HLB values of 6.3 and 6.2, respectively) with Comparative Example C5 (prepared with HS-1 having a glycerol monolaurate content of 44.5% and a calculated HLB value of 4.3). The samples shown in Examples 6 and 11 provided improved wettability over the control. However, the Comparative Example C5 sample did not. In part, this was attributable to the lower concentration of monoglyceride in the Comparative C5 sample. Also, even quite pure materials, like GM-C18 (87% glycerol monomyristate, HLB value of 3.0), are not as effective at imparting wettability to the nonwoven web as monoglycerides derived from carboxylic acids with optimum chain lengths. Thus, the HLB value which accounts for both monoglyceride content and type of monoglyceride can be an excellent predictor of whether commercially available monoglyceride, diglyceride, triglyceride and glycerol mixtures will function at the concentrations most desired for cost effectiveness and processability. The data show that additive materials containing monoglycerides and having HLB values of about 4.5 to 9.0 will improve wettability over the control.

HS-5 and HS-6 which are mixtures of di- and mono-fatty acid esters of polyethylene glycol, did not significantly improve the wettability of nonwoven webs over the control.

Examples 14 to 18 and Comparative Examples C16 to C20

In Examples 14 to 18 and Comparative Examples $C_{16}$ to C20, polybutylene (PB 0400) was evaluated as a hydrophilic enhancer for various hydrocarbon surfactants. In all Examples and Comparative Examples, polypropylene EOD 96-36 and the Melt-Blown Extrusion Procedure A were used to prepare the nonwoven web samples and the Hydrophilicity Test was used to evaluate the initial wettability of each of the nonwoven webs.

A description of the samples and their results from the Hydrophilicity Test are Table 3.

TABLE 3

| Ex. | Hydrocarbon Surfactant (wt. %) | PB 0400 (wt. %) | Cold Water: Rating | Hot Water: Rating |
|---|---|---|---|---|
| 14 | GML (1.0%) | 5 | 3.6 | 1 |
| 14 control | GML (1.0%) | — | 5 | 3.4 |
| 15 | GML (1.5%) | 5 | 1 | 1 |
| 15 control | GML (1.5%) | — | 2.3 | 1.3 |
| 16 | GML (2.0%) | 5 | 1 | 1 |
| 16 control | GML (2.0%) | — | 1.4 | 1 |
| C16 | HS-1 (1.5%) + HS-7 (1.5%) | 5 | 5 | 4.8 |
| C16 Control | HS-1 (1.5%) + HS-7 (1.5%) | — | 5 | 5 |
| C17 | HS-3 (1.5%) + HS-7 (1.5%) | 5 | 5 | 2.9 |
| C17 Control | HS-3 (1.5%) + HS-7 (1.5%) | — | 5 | 4.4 |

TABLE 3-continued

| Ex. | Hydrocarbon Surfactant (wt. %) | PB 0400 (wt. %) | Cold Water: Rating | Hot Water: Rating |
|---|---|---|---|---|
| C18 | HS-1 (3.0%) | 5 | 5 | 2.3 |
| C18 Control | HS-1 (3.0%) | — | 5 | 4.3 |
| 17 | GM-C12 (2.0%) | 5 | 1 | 1 |
| 18 | GM-C14 (3.0%) | 5 | 2 | 1 |
| C19 | GM-C18D (2.0%) | 5 | 4.5 | 2 |
| C20 | HS-7 (3.0%) | — | 5 | 5 |
| C20 Control | HS-7 (3.0%) | 5 | 5 | 5 |

The data in Table 3 show that polybutylene enhanced the wettability of the polypropylene webs containing glycerol monoesters with HLB values ranging from 5.3 to 8.3 versus the controls (no polybutylene). Polybutylene did not significantly enhance wettability when combined with glycerol monoesters having HLB values of less than 5 in combination with an ethoxylated alkylphenol surfactant. Polybutylene also did not enhance the wettability of webs prepared using only an ethoxylated octylphenol surfactant.

Re-testing of Selected Webs from Tables 1 and 2 after Aging at Room Temperature

The nonwoven webs from Examples 6, 8, 10, 14, 15, 16 and 17 were reevaluated for wettability using the Hydrophilicity Test after aging under ambient lab conditions for a period of 4–5 months (also after 2 months for Examples 6 and 15). The wetting values, initially and after aging, are presented in Table 4.

TABLE 4

| Ex. | Hydrocarbon Surf. (wt. %) | PB 0400 (wt. %) | Cold Water (initial and after aging) | | | Hot Water (initial and after aging) | | |
|---|---|---|---|---|---|---|---|---|
| | | | Init. | 2 mos. | 4–5 mos | Init. | 2 mos. | 4-5 mos. |
| 6 | GML (3.0%) | — | 1 | 3 | 4 | 1 | 1 | 1 |
| 8* | GML (3.0%) | — | 1 | N/R | 5 | 1 | N/R | 1 |
| 10* | GM-C10 (3.0%) | — | 1 | N/R | 3 | 1 | N/R | 1 |
| 14 | GML (1.0%) | 5.0 | 3.6 | N/R | 4 | 1 | N/R | 1 |
| 15 | GML (1.5%) | 5.0 | 1 | 4 | 4 | 1 | 1 | 1 |
| 16 | GML (2.0%) | 5.0 | 1 | N/R | 4 | 1 | N/R | 1 |
| 17 | GM-C12 (2.0%) | 5.0 | 1 | N/R | 5 | 1 | N/R | 1 |

*: means extruded at 220° C. rather than the usual 270–280° C.
N/R: means not recorded The data in Table 4 show that the wettability of the polypropylene webs to cold water decreased after storage for 4–5 months, even when polybutylene was present.

Examples 19–23 and Comparative Examples C21–C23

A series of experiments was run to investigate the effect of using SPAN™ 20 (sorbitan monolaurate) or SPAN™ 40 (sorbitan monopalmitate) in combination with GML and polypropylene to improve the hydrophilicity of the extruded webs after aging. In all Examples and Comparative Examples, polypropylene EOD 96-36 and the Melt-Blown Extrusion Procedure A were used to prepare the nonwoven web samples and the Hydrophilicity Test was used to evaluate the wettability of each nonwoven web, both initially and after aging for 23 days under ambient conditions.

TABLE 5

| Ex. | wt % GML | wt %: Span 20 | wt %: Span 40 | Cold Water Init. | Cold Water After Aging 23 days | Hot Water: Init. | Hot Water: After Aging 23 days |
|---|---|---|---|---|---|---|---|
| C21 | — | — | — | 5 | 5 | 5 | 5 |
| 19 | 3 | — | — | 1 | 4 | 1 | 1 |
| 20 | 2.25 | 0.75 | — | 1 | 1 | 1 | 1 |
| 21 | 1.5 | 1.5 | — | 5 | 2.7 | 1 | 1 |
| C22 | — | 3.0 | — | 5 | 4 | 1.7 | 1 |
| 22 | 2.25 | — | 0.75 | 1 | 1 | 1 | 1 |
| 23 | 1.5 | — | 1.5 | 2.7 | 1 | 2 | 1 |
| C23 | — | — | 3.0 | 5 | 3.3 | 5 | 4 |

The data in Table 5 show that GML in combination with either SPAN™ 20 or SPAN™ 40 produced nonwoven webs with superior hydrophilicity after aging. Optimum hydrophilicy before and after aging occurred at 25% replacement of the GML with either SPAN™ 20 or SPAN™ 40. Also, SPAN™ 20 and SPAN™ 40 acted as an extender, allowing for 25% substitution of the more expensive GML component.

Examples 24–32 and Comparative Examples C24-C25

A series of experiments was run to investigate mixtures of PB 0400 polybutylene, various sorbitan esters, and GML as polymer melt additives for polypropylene. In all Examples and Comparative Examples, polypropylene EOD 96-36 and the Melt-Blown Extrusion Procedure A were used to prepare the nonwoven web samples, and the Hydrophilicity Test was used to evaluate the wettability of each nonwoven web, both initially and after aging under ambient conditions. The web samples containing SPAN™ 20 (sorbitan monolaurate) were aged for 10 days at room temperature, while the web samples containing ARLACEL™ 60 (sorbitan monostearate) and ARLACEL™ 83 (sorbitan sequioleate) were aged for 7 days at room temperature.

Results from the Hydrophilicity Test are presented in Table 6.

TABLE 6

| Ex. | GML wt % | Sorbitan Ester (SPAN ®/ARLACEL ®): Product Number | Sorbitan Ester (SPAN ®/ARLACEL ®): wt % | PB0400 wt % | Cold Water: Init. | Cold Water: After Aging | Hot Water: Init. | Hot Water: After Aging |
|---|---|---|---|---|---|---|---|---|
| 24 | 1.8 | 20 | 0.2 | — | 1.7 | 3.7 | 1 | 1 |
| 25 | 1.8 | 20 | 0.2 | 5 | 1 | 3 | 1 | 1 |
| 26 | 1.4 | 20 | 0.6 | — | 1.7 | 3.7 | 1 | 1.7 |
| 27 | 1.4 | 20 | 0.6 | 5 | 1 | 2 | 1 | 1 |
| 28 | 2.1 | 20 | 0.9 | — | 1 | 3 | 1 | 1 |
| 29 | 2.1 | 20 | 0.9 | 5 | 1 | 2 | 1 | 1 |
| 30 | 1.05 | 60 | 0.45 | 5 | 3.3 | 4 | 1 | 1 |
| C24 | — | 60 | 1.5 | 5 | 5 | 5 | 5 | 5 |
| 31 | 1.05 | 83 | 0.45 | 5 | 3.3 | 4 | 1 | 1 |
| C25 | — | 83 | 1.5 | 5 | 3.7 | 5 | 2 | 2 |
| 32 | 1.05 | 20 | 0.45 | 11.58 | 1 | N/R | 1 | N/R |
| 32A | 0.975 | 20 | 0.525 | 7.5 | 2 | N/R | 1.2 | N/R |
| 32B | 0.975 | 20 | 0.525 | 3.5 | 3.7 | N/R | 3 | N/R |
| 14 | 1 | — | — | 5 | 3.6 | — | 1 | — |

N/R = not run

The data in Table 6 show that the addition of 5% polybutylene to blends of GML and SPAN™ 20 generally improved the cold water hydrophilicity of the web, both before and after aging. Neither ARLACEL™ 60 or ARLACEL™ 83 appeared to offer any particular benefit when incorporated with the GML (compare initial results from Examples 30 and 31 with example 14 included for reference). GML levels could be reduced to nearly 1% when the PB 0400 level was increased to greater than 10% and the SPAN™ 20 level was under 0.5% (Example 32).

The aged webs from Example 30 and Comparative Example C24 were tested again according to the Hydrophilicity Test after aging for a total of about 7 months. Hot water values were 2 and 5, respectively, while cold water values were 5 and 5, respectively.

Examples 33–49 and Comparative Example C26

A series of experiments was run to investigate the optimum weight ratio of GML to SPAM™ 20 or SPAN™ 40 when used in conjunction with 5% PB 0400 polybutylene as a polymer melt additive to polypropylene. In all Examples and the Comparative Example, polypropylene EOD 96-36 and the Melt-Blown Extrusion Procedure A were used to prepare the nonwoven web samples and the Hydrophilicity Test was used to evaluate the wettability of each nonwoven web, both initially and after aging for 10 days under ambient conditions.

Results from the Hydrophilicity Test are presented in Table 7.

TABLE 7

| Ex. | GML + SPAN ™ monoester wt % | SPAN ™ monoester Product No. | GML to SPAN ™ monoester Ratio | PB0400 wt % | Cold Water: Init. | Cold Water: After Aging 10 days | Hot Water: Init. | Hot Water: After Aging 10 days |
|---|---|---|---|---|---|---|---|---|
| C26 | — | — | — | — | 5 | 5 | 5 | 5 |
| 33 | 3 | — | infinite | — | 1 | 3.8 | 1 | 1 |
| 34 | 2 | 20 | 90/10 | 5 | 1 | 3.8 | 1 | 1 |
| 35 | 2 | 20 | 70/30 | 5 | 1 | 1 | 1 | 1 |
| 36 | 1.75 | 20 | 90/10 | 5 | 1 | 5 | 1 | 1 |
| 37 | 1.75 | 20 | 50/50 | 5 | 1 | 1 | 1 | 1 |

TABLE 7-continued

| Ex. | GML + SPAN™ monoester wt % | SPAN™ monoester Product No. | GML to SPAN™ monoester Ratio | PB0400 wt % | Cold Water: Init. | Cold Water: After Aging 10 days | Hot Water: Init. | Hot Water: After Aging 10 days |
|---|---|---|---|---|---|---|---|---|
| 38 | 1.5 | 20 | 70/30 | 5 | 1 | 1 | 1 | 1 |
| 39 | 1.5 | 20 | 50/50 | 5 | 1 | 1 | 1 | 1 |
| 40 | 1 | 20 | 90/10 | 5 | 1 | 4 | 1 | 1 |
| 41 | 1 | 20 | 70/30 | 5 | 1 | 1 | 1 | 1 |
| 42 | 1 | 20 | 50/50 | 5 | 1 | 1 | 1 | 1 |
| 43 | 2 | 40 | 90/10 | 5 | 1 | 2 | 1 | 1 |
| 44 | 2 | 40 | 50/50 | 5 | 3 | 4 | 1 | 1 |
| 45 | 1.75 | 40 | 90/10 | 5 | 1 | 2.7 | 1 | 1 |
| 46 | 1.75 | 40 | 70/30 | 5 | 1 | 3 | 1 | 1 |
| 47 | 1.5 | 40 | 90/10 | 5 | 1 | 4 | 1 | 1 |
| 48 | 1.5 | 40 | 70/30 | 5 | 1 | 1.7 | 1 | 1 |
| 49 | 1.5 | 40 | 50/50 | 5 | 2 | 2.7 | 1 | 1 |

The data in Table 7 shows that, in a 1–2% concentration range of GML plus SPAN™ monoester, replacement of GML with 10% of SPAN™ 20 monoester does not greatly improve the cold water hydrophilicity after aging of the meltblown webs. However, replacement of GML with 30% or 50% of SPAN™ 20 monoester clearly enhances the cold water hydrophilicity after aging of the webs. Additionally, SPAN™ 20 monoester is more effective than SPAN™ 40 monoester in improving the cold water hydrophilicity after aging of the webs.

Examples 50–69 and Comparative Examples C27–C29

A ladder experiment was run to determine the effective use levels of GML, SPAN™ 20 (SML) and PB 0400 polybutylene (PB) in EOD 96-36 polypropylene. GML levels were varied from 0–2% and SPAN™ 20 levels were varied from 0–2% so that the total of the two levels was kept at 2%. Meanwhile, the level of PB was kept constant at 7.5% in all cases except for Comparative Example C29, which was run with polypropylene alone. Extrusion was done using Melt-Blown Extrusion Procedure A, and the resulting webs were evaluated for hydrophilicity using the Hydrophilicity Test (both Cold Water and Hot Water) and the Percent Wet Pickup Test, both described above. Web samples were evaluated initially and after aging for 2000 hours at room temperature. Results from these evaluations are presented in Table 8.

TABLE 8

| Ex. | % GML | % SML | % PB | Percent Wet Pickup: Initial | Percent Wet Pickup: Aged | Cold Water: Init. | Cold Water: Aged | Hot Water: Init. | Hot Water: Aged |
|---|---|---|---|---|---|---|---|---|---|
| 50 | 2.0 | — | 7.5 | 745 ± 44 | 238 ± 23 | 1 | 4 | 1 | 1 |
| 51 | 1.9 | 0.1 | 7.5 | 809 ± 30 | 276 ± 70 | 1 | 4 | 1 | 1 |
| 52 | 1.8 | 0.2 | 7.5 | 773 ± 33 | 174 ± 34 | 1 | 4 | 1 | 1 |
| 53 | 1.7 | 0.3 | 7.5 | 749 ± 24 | 369 ± 41 | 1 | 3 | 1 | 1 |
| 54 | 1.6 | 0.4 | 7.5 | 751 ± 22 | 298 ± 47 | 1 | 3 | 1 | 1 |
| 55 | 1.5 | 0.5 | 7.5 | 749 ± 32 | 268 ± 23 | 1 | 3 | 1 | 1 |
| 56 | 1.4 | 0.6 | 7.5 | 753 ± 30 | 490 ± 48 | 1 | 2 | 1 | 1 |
| 57 | 1.3 | 0.7 | 7.5 | 1004 ± 17 | 666 ± 64 | 1 | 2 | 1 | 1 |
| 58 | 1.2 | 0.8 | 7.5 | 711 ± 14 | 627 ± 46 | 1 | 1 | 1 | 1 |
| 59 | 1.1 | 0.9 | 7.5 | 838 ± 104 | 709 ± 23 | 1 | 1 | 1 | 1 |
| 60 | 1.0 | 1.0 | 7.5 | 800 ± 28 | 615 ± 15 | 1 | 1 | 1 | 1 |
| 61 | 0.9 | 1.1 | 7.5 | 831 ± 25 | 563 ± 18 | 1 | 1 | 1 | 1 |
| 62 | 0.8 | 1.2 | 7.5 | 878 ± 40 | 644 ± 16 | 2 | 1 | 1 | 1 |
| 63 | 0.7 | 1.3 | 7.5 | 868 ± 37 | 641 ± 20 | 1 | 2 | 1 | 1 |
| 64 | 0.6 | 1.4 | 7.5 | 737 ± 112 | 665 ± 38 | 4 | 1.7 | 2 | 1 |
| 65 | 0.5 | 1.5 | 7.5 | 626 ± 55 | 655 ± 27 | 4 | 1 | 2 | 1 |
| 66 | 0.4 | 1.6 | 7.5 | 229 ± 36 | 605 ± 16 | 4 | 1.3 | 3 | 1 |
| 67 | 0.3 | 1.7 | 7.5 | 188 ± 43 | 706 ± 17 | 5 | 1.3 | 3 | 1 |
| 68 | 0.2 | 1.8 | 7.5 | 247 ± 68 | 568 ± 10 | 5 | 2.3 | 3 | 1.3 |
| 69 | 0.1 | 1.9 | 7.5 | 162 ± 31 | 659 ± 43 | 5 | 3 | 5 | 1.7 |
| C27 | — | 2.0 | 7.5 | 118 ± 37 | 381 ± 15 | 5 | 4.3 | 4 | 2 |
| C28 | — | — | 7.5 | 6 ± 4 | 11 ± 8 | 5 | 5 | 5 | 5 |
| C29 | — | — | — | 9 ± 6 | 15 ± 20 | 5 | 5 | 5 | 5 |

Based on the results from both tests, the data in Table 8 show that substitution of GML with at least 15% SPAN™ 20 led to improvement in cold water absorption after the web sample had aged. Based on the Hydrophilicity Test results, overall optimum wetting seemed to occur when about 40–60% of the GML was substituted with SPAN™ 20. Interestingly, hydrophilicity often improved after aging in web samples containing higher percentages of SPAN™ 20.

Examples 70 to 72

In Examples 70 to 72, compositions containing both GML and HS-1 (glycerol monolaurates of high and low purity, respectively) at various weight ratios were evaluated in polypropylene EOD 96-36 using Melt-Blown Extrusion Procedure A. The Hydrophilicity Test was used to evaluate the wettability of each nonwoven web. A description of the hydrocarbon surfactant compositions, their monoglyceride content, calculated HLB values and wettability data are presented in Table 9.

TABLE 9

| Example | Hydrocarbon Surfactants and Amounts (wt. %) | Monoglyceride (wt. %) | Cold Water Rating | Hot Water Rating | HLB Value Surfactant |
|---|---|---|---|---|---|
| 70 | (1.5%) GML + (1.5%) HS-1 | 69.25 | 4.5 | 2 | 5.3 |
| 71 | (2.25%) GML + (0.75%) HS-1 | 81.625 | 2.2 | 1 | 5.8 |
| 72 | (2.44%) GML + (0.56%) HS-1 | 84.71 | 2 | 1 | 5.93 |

The data in Table 9 show that very good cold water wettability can be achieved using the described combinations of surfactants provided the overall HLB values of the surfactant combinations were kept between about 5.8 and 5.93 (corresponds to a monoglyceride content of at least 81.6 wt. % and 84.7 wt. % respectively).

Examples 73 to 75 and Comparative Example C30

Four films were produced from the nonwoven webs of Examples 6 and 15, and Comparative Examples C5 and C15. The fabrics were melted at 200° C. in a platen press and then pressed with an applied force of ten tons for about 45 seconds. The samples were then allowed to air cool under the same pressure. The resulting films were all seven mils (0.3 mm) thick.

A test was run to determine the anti-fog properties of the four sample films. The test was performed as follows: Firstly, four four-ounce glass jars were filled with warm water (approximately 30° C. ) to just below the neck. A silicone sealant (Cling 'n Seal RTV silicone adhesive/sealant) was applied to the top of the jar. Each film sample was placed on top of a jar to act as a lid, and then the four jars were left for fifteen minutes at ambient conditions to let the sealant set up. All of the film samples with jars were then placed into an oil-bath that was heated to 50° C. Data were then collected periodically as to amount of water that had collected on the bottom of each film. Results are shown in Table 10.

The data in Table 10 show that one cannot distinguish the anti-fog properties in films containing HS-1 at 3%, GML at 3%, and GML at 1.5%+5% Shell PB0400 polybutylene. However, data on the cold water wettability of webs prepared using the same extrudable compositions (see Table 2) show that the wettability of webs prepared from compositions containing 3% GML or 1.5% GML+5% Polybutylene PB 0400 had a significantly better cold water wetting rating (i.e., 1) than a web prepared from a composition containing 3% HS-1 (i.e., 5).

Example 76

This Example illustrates the preparation of an absorbent device according to the invention. A melt-blown nonwoven web of polypropylene was prepared from a polymer/monoester blend of Fina 3960X polypropylene and 3.0% by weight of GML using the Melt Blown Extrusion Process B, described herein. The resulting web (basis weight 130 g/m$^2$) was combined with cellulose pulp (basis weight 40 g/m$^2$) commercially available from International Tray Pads and Packaging, Inc. of Aberdeen, N.C. as 7 ply Hibulk Paper Web using a process similar to that described in U.S. Pat. No. 4,100,324 (which disclosure is incorporated by reference herein) to give a finished nonwoven absorbent web material.

A three-layer absorbent device was then prepared by laminating together the above finished web material with a liquid-impermeable polypropylene backing sheet prepared according to the method described in U.S. Pat. No. 4,726,989 (Mrozinski), (Example 1 without the solvent extraction of the oil) on one side and a liquid-permeable non-stick netting (CKX215 P-S Netting, commercially available from Applied Extrusion Technologies, Middletown, Del.) on the other side. The lamination was carried out using hexagonal honeycomb patterned rolls heated to 132° C. and gapped at 0.12 to 0.25 mm. The dressing was observed to immediately absorb body-temperature water on the side with the non-stick netting.

Examples 77 to 81

These Examples illustrate the antimicrobial activity of nonwoven webs used to prepare the absorbent devices.

Melt-blown nonwoven webs were prepared using PP3505 polypropylene and various amounts of GML using a process similar to the Melt-Blown Extrusion Process B except with a flow rate of 0.45 Kg/hr and a temperature range of 250° C. to 280° C. In the case of Example 77, the resulting web was further combined with cellulose pulp using a process and a material similar to that described in Example 76. In Example 81, following extrusion of the hot polymeric fibers, an aqueous solution of LA was sprayed onto the fibers to achieve a level of 1.5% (based on the total weight of the

TABLE 10

| | Film Sample | Condensation on Film at Designated Time | | | |
|---|---|---|---|---|---|
| Example | Components and Amounts (wt. %) | 5 min. | 30 min. | 1 hr. | 2 hrs. |
| C30 | (100%) Polypropylene Control | Fogged over with vapor | Fine drops | Small drops | Small drops |
| 73 | (97%) Polypropylene + (3%) HS-1 | Very fine drops | Small drops | Large drops | Large drops |
| 74 | (97%) Polypropylene + (3%) GML | Small drops | Large drops | Large drops | Large drops |
| 75 | (93.5%) Polypropylene + (1.5%) GML + (5%) Polybutylene PB 0400 | Large drops | Large drops | Large drops | Large drops | coated and dried web). The heat of the polymer evaporated the water and left the lactic acid intimately in contact with the GML-containing fibers.

The resulting webs were then evaluated for antimicrobial activity using the Antimicrobial Test and *Staphylococcus aureus*. The concentrations of GML used to prepare the Examples, the web basis weights and the web antimicrobial activities are summarized in Table 11. The antibacterial data in Table 11 are percent reductions in bacterial colony forming units (CFU) after a 24-hour exposure time at 23–24° C. These data show that all test samples possessed bactericidal activity although the material treated with lactic acid after extrusion showed the greatest percent kill of *S. aureus*.

TABLE 11

| Example | GML (%) | Lactic Acid (%) | Reduction of Bacterial CFU (%) | Web Basis Wt. (g/m²) |
|---|---|---|---|---|
| 77 | 2.0 | 0 | 98.63 | 103 |
| 78 | 2.0 | 0 | 99.91 | 68 |
| 79 | 1.0 | 0 | 96.83 | 52 |
| 80 | 1.5 | 0 | 94.48 | 52 |
| 81 | 2.0 | 1.5 | 99.99 | 65 |

Examples 82–86

These Examples illustrate the degree of water absorbency of various nonwoven web constructions of this invention.

In Examples 82–84, melt-blown polypropylene nonwoven webs were prepared using PP3505 polypropylene and various amounts of GML using a process similar to the Melt-Blown Extrusion Process B, except that the monoester throughput rate was about 6.8 kg/hr and the die width was about 51 cm.

In Example 85, a melt-blown polypropylene nonwoven web was prepared using PP3746 polypropylene, 7.5% PB 0400 polybutylene, and 2.0% GML using a process similar to the Melt-Blown Extrusion Process B, except that the monoester throughput rate was about 9.1 kg/hr and the die width was about 51 cm.

In Example 86, a sample of the three-layer absorbent device prepared as generally described in Example 76 was employed. The nonwoven polypropylene web component was made using 3.0% GML and had a resulting basis weight of 130 g/m². The average dry weights of the individual components of a 7.62 cm×7.62 cm sample of the device were 0.16 g (netting), 0.13 g (film backing), and 0.96 g (absorbent polypropylene/cellulose pulp core).

The amount of water absorbed, and the percent water absorbency of 7.62 cm×7.62 cm samples of Examples 82–86 were measured according to the Percent Water Absorbency Test described above. Results are provided in Table 12.

TABLE 12

| Example | GML (%) | Water Absorbed (g) | Percent Water Absorbency (%) |
|---|---|---|---|
| 82 | 3.0 | 10.29 | 1278 |
| 83 | 4.0 | 9.62 | 1177 |
| 84 | 5.0 | 10.14 | 1254 |
| 85 | 2.0 | 9.90 | 1127 |
| 86 | 3.0 | 11.47 | 919* |

*Percent Water Absorbency = 1211% based on dry weight of the device less the dry weight of netting and film components.

The data in Table 12 show that all samples were highly water absorbent with each sample capable of absorbing over ten times its own weight with water. For these Examples, there was not a significant correlation between % water absorbency and levels of GML present in the samples.

Examples 87–89 and Comparative Example C31

These examples illustrate the hydrophilicity of various spunbond fabrics of this invention.

Using the Spunbond Extrusion Procedure with minor modifications, spunbond fabrics containing various percentages of GML, PB 0400 polybutylene and/or SPAN™ 20 in EXXON™ 3155 polypropylene were prepared.

In Example 87, the extruded polymer mixture consisted of 93.5% 3155, 1.5% GML and 5% PB 0400.

In Example 88, the extruded polymer mixture consisted of 88.5% 3155, 1.05% GML, 0.45% SPAN™ 20 and 10% PB 0400.

In Example 89, the extruded polymer mixture consisted of 86.2% 3155, 1.65% GML, 0.85% SPAN™ 20 and 11.33% PB 0400.

In Comparative Example C3 1, the extruded polymer mixture consisted of 95% 3155 and 5% PB 0400 (no hydrophilic additive).

The fabrics were tested for hydrophilicity using the Drop Wetting Test. Results from these tests are shown below in Table 13.

TABLE 13

| Processing Conditions: | Ex. 87 | Ex. 88 | Ex. 89 | C. Ex. C31 |
|---|---|---|---|---|
| Melt Temp. (° C.) | 199 | 207 | 227 | 196 |
| Throughput (g/hole/min) | 0.15 | 0.15 | 0.25 | 0.15 |
| Basis Weight (g/m²) | 20 | 20 | 17 | 20 |
| No. of Drops/10 Absorbed | 3 | 5 | 4 | 0 |

The data in Table 13 show that all of the spunbond samples containing GML (Examples 87–89) demonstrated hydrophilicity, while the sample without the GML (Comparative Example C31) was hydrophobic.

Examples 90–109 and Comparative Example C32

These examples illustrate the use of various polymer additives at the 10% level to improve the hydrophilicity of melt-blown web samples made of EOD 96-36 polypropylene containing GML and 70/30 blends of GML/PAN™. Extrusion was done using Melt-Blown Extrusion Procedure A, and the resulting web samples were evaluated for initial hydrophilicity to hot and cold water using the Hydrophilicity Test. Results from these evaluations are presented in Table 14.

TABLE 14

| Ex. | % GML | % SPAN ™ 20 | Polymer Additive | Cold Water | Hot Water |
|---|---|---|---|---|---|
| C32 | — | — | — | 5 | 5 |
| 90 | 1 | — | — | 4.3 | 5 |
| 91 | 1.25 | — | — | 4.3 | 3.6 |
| 92 | 1.5 | — | — | 2 | 3 |
| 93 | 2 | — | — | 1.3 | 1.7 |
| 94 | 2 | — | PB 0400 | 1 | 1 |
| 95 | 1.25 | — | PB 0400 | 1 | 1 |
| 96 | 1.25 | — | DP-8340 | 1 | 1 |
| 97 | 1.25 | — | 8401 | 1 | 1 |
| 98 | 1.25 | — | 8402 | 1 | 1 |
| 99 | 1.25 | — | 4023 | 1 | 1 |

TABLE 14-continued

| Ex. | % GML | % SPAN ™ 20 | Polymer Additive | Cold Water | Hot Water |
|---|---|---|---|---|---|
| 100 | 1.25 | — | 8910 | 1 | 1 |
| 101 | 1.4 | 0.6 | — | 2 | 2.3 |
| 102 | 1.23 | 0.52 | — | 2.3 | 3 |
| 103 | 1.05 | 0.45 | — | 2.3 | 3 |
| 104 | 1.05 | 0.45 | PB 0400 | 1 | 1 |
| 105 | 1.05 | 0.45 | DP-8340 | 1 | 1.2 |
| 106 | 1.05 | 0.45 | DP-8910 | 1 | 1 |
| 107 | 1.05 | 0.45 | 4023 | 1 | 1 |
| 108 | 1.05 | 0.45 | 8401 | 1 | 1 |
| 109 | 1.05 | 0.45 | 8402 | 1 | 1 |

The data in Table 14 shows that the polyolefinic hydrophilic enhancers all improved the hydrophilicity of the nonwoven web samples.

The complete disclosures of the patents, patent documents, and publications cited herein hereby incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited solely by the claims set forth herein as follows.

We claim:

1. A wound dressing comprising:

(a) an absorbent layer comprising hydrophilic polypropylene fibers having incorporated therein an amount of a $C_8$ to $C_{16}$ fatty acid monoglyceride effective to alone render the fibers hydrophilic;

(b) a liquid-impermeable and moisture vapor-permeable backing sheet adhered to an outer surface of the absorbent layer; the backing sheet substantially coextensive with the absorbent layer; and (c) a liquid-permeable sheet that is substantially coextensive with an adhered to the surface of the absorbent layer opposite the surface to which the backing sheet is adhered.

2. The wound dressing of claim 1 wherein the absorbent layer further includes an absorbent additive.

3. The wound dressing of claim 2 wherein the absorbent additive is selected from the group consisting of wood pulp, cellulose, cotton, rayon, recycled cellulose, shredded cellulose sponge, and mixtures thereof.

4. The wound dressing of claim 2 wherein the monoglyceride is a glycerol monolaurate and the absorbent additive is wood pulp.

5. The wound dressing of claim 1 further comprising a hydrophilic enhancer material.

* * * * *